United States Patent
Serex et al.

(10) Patent No.: US 12,144,982 B2
(45) Date of Patent: Nov. 19, 2024

(54) STRETCHABLE CUFF DEVICE

(71) Applicant: ECOLE POLYTECHNIQUE FEDERALE DE LAUSANNE (EPFL), Lausanne (CH)

(72) Inventors: Ludovic Serex, Lausanne (CH); Nicolas Vachicouras, Chambésy (CH); Florian Fallegger, Lausanne (CH); Giuseppe Schiavone, Morges (CH); Valentina Marie Paggi, Chavannes-près-Renens (CH)

(73) Assignee: ECOLE POLYTECHNIQUE FEDERALE DE LAUSANNE, (EPFL) Lausanne (CH)

( * ) Notice: Subject to any disclaimer, the term of this patent is extended or adjusted under 35 U.S.C. 154(b) by 273 days.

(21) Appl. No.: 17/613,538

(22) PCT Filed: Jun. 9, 2020

(86) PCT No.: PCT/IB2020/055395
§ 371 (c)(1),
(2) Date: Nov. 23, 2021

(87) PCT Pub. No.: WO2020/254915
PCT Pub. Date: Dec. 24, 2020

(65) Prior Publication Data
US 2022/0249834 A1    Aug. 11, 2022

(30) Foreign Application Priority Data

Jun. 18, 2019   (WO) .................. PCT/IB2019/055101

(51) Int. Cl.
*A61N 1/36*   (2006.01)
*A61B 5/388*   (2021.01)
*A61N 1/05*   (2006.01)

(52) U.S. Cl.
CPC ............ *A61N 1/0556* (2013.01); *A61B 5/388* (2021.01); *A61N 1/0509* (2013.01); *A61N 1/0558* (2013.01); *A61N 1/3606* (2013.01)

(58) Field of Classification Search
CPC .. A61N 1/0556; A61N 1/0509; A61N 1/0558; A61N 1/3606; A61N 1/36003;
(Continued)

(56) References Cited

U.S. PATENT DOCUMENTS

2004/0192082 A1   9/2004  Wagner et al.
2009/0227831 A1*  9/2009  Burnett ................ A61N 1/3603
                                                600/13
(Continued)

FOREIGN PATENT DOCUMENTS

| WO | WO 2004095536 | 11/2004 |
| WO | WO 2016/110564 | 7/2016 |
| WO | WO 2018/100005 | 6/2018 |

OTHER PUBLICATIONS

Cobo, A. M., Larson, C. E., Scholten, K., Miranda, J. A., Elyahoodayan, S., Song, D., . . . & Meng. E. (2018). Parylene-based cuff electrode with integrated microfluidics for peripheral nerve recording, stimulation, and drug delivery. Journal of Microelectromechanical Systems, 28(1), 36-49.
(Continued)

*Primary Examiner* — Yingchuan Zhang
*Assistant Examiner* — Anh-Khoa N Dinh
(74) *Attorney, Agent, or Firm* — NIXON & VANDERHYE

(57) ABSTRACT

The invention features a cuff device comprising a support having a first end, a second end and an elongated body in between; connection means for electrical, magnetic and/or fluidic magnetic connection with external devices; at least one of i) an electrode and/or electronic component opera-
(Continued)

tively connected with said connection means configured to electrically interface with a biological tissue and ii) a channel having an inlet, an outlet and an elongated body in between operatively connected with said connection means via said inlet and configured to fluidically interface with a biological tissue via said outlet; and at least one buckle configured to receive said first end and permit the sliding therein of said elongated body so to close and lock the cuff electrode device at desired positions, characterized in that said support is stretchable.

19 Claims, 11 Drawing Sheets

(58) Field of Classification Search
CPC ............ A61N 1/36007; A61N 1/36017; A61N 1/36046; A61N 1/36053; A61N 1/36057; A61N 1/36062; A61N 1/36064; A61N 1/36078; A61N 1/36103; A61B 5/388; A61B 5/24
See application file for complete search history.

(56) References Cited

U.S. PATENT DOCUMENTS

| | | |
|---|---|---|
| 2018/0001081 A1 | 1/2018 | Minev et al. |
| 2020/0094466 A1 | 3/2020 | Vachicouras et al. |

OTHER PUBLICATIONS

International Search Report mailed on Sep. 21, 2020, for Application N° PCT/IB2020/055395.
Rosset, S., & Shea, H. R. (2013). Flexible and stretchable electrodes for dielectric elastomer actuators. Applied Physics A, 110(2), 281-307.
Seki, Y., Yamagiwa, S., Morikawa, Y., Sawahata, H., Numano, R., Ishida, M., & Kawano, T. (2017, January). Hook and loop microfastener: flexible microelectrodes tied to a nerve. In 2017 IEEE 30th International Conference on Micro Electro Mechanical Systems (MEMS) (pp. 117-120). IEEE.
Written Opinion of the ISA mailed on Sep. 21, 2020, for Application N° PCT/IB2020/055395.
Yu, H., Xiong, W., Zhang, H., Wang. W., & Li, Z. (2014). A parylene self-locking cuff electrode for peripheral nerve stimulation and recording. Journal of Microelectromechanical Systems, 23(5), 1025-1035.

* cited by examiner

STRETCHABLE CUFF DEVICE

CROSS-REFERENCE TO RELATED APPLICATIONS

The present patent application is an United States national stage application of International Patent Application with the Application Serial No. PCT/IB2020/055395 that was filed on Jun. 9, 2020 designating the United States, and claims foreign priority to International Patent Application with the Application Serial No. PCT/IB2019/055101 that was filed on Jun. 18, 2019, the entire contents of these two documents herewith incorporated by reference in their entirety.

TECHNICAL FIELD

The invention belongs to the fields of stretchable electronics and stretchable medical devices. In particular, the invention relates to stretchable cuff devices useable as compliant, soft body interfaces or implants.

BACKGROUND ART

Electrode arrays are medical devices that can be used as electrical interfaces to record and/or stimulate various biological tissues to treat or diagnose various diseases. These can be placed for example on the central nervous system, peripheral nervous system, muscles (such as the heart or the gut), or on the skin. There have been multiple developments over the years to interface these devices with various anatomical targets in the body.

Electrical stimulation of nerves, nerve fibers etc, has been intensively studied in an effort to e.g. activate muscles. In this context, nerve cuff electrodes are being used for applying electrical stimulation to peripheral nerves. Such prior art nerve cuffs are configured to be wrapped around a nerve and are provided with a number of discrete electrodes in the form of surface electrodes that can contact the nerve, i.e. the surface of the peripheral nerve trunk at different positions, thus allowing to stimulate said nerve and/or record signals from it. Multiple implementations of cuff electrodes have been devised depending upon the diameter of the nerve that needs to be addressed and on the technology used to fabricate the cuff. Generally, such cuff electrodes are implanted around a subject's nerve by two main procedures, namely the sliding of the cuff structure along a resected nerve or the wrapping and locking of a previously opened flat structure around a nerve, such as with the use of so-called split-cylinder cuff electrodes. The main drawback of split-cylinder cuff electrodes is that the rigid cuff of a fixed diameter must be properly fitted for each nerve. A relatively small cuff may cause the nerve compression induced injury during chronic implantation.

Yu, H., Xiong et al. (J. Microelectromechanical Syst. 23, 1025-1035, 2014) disclosed a microfabricated, parylene-based self-locking cuff electrode. The cuff diameter can be adjusted to accommodate the nerve properly during implantation and can be locked similarly to a cable tie using a buckle implementation to secure the cuff. The self-locking cuff electrode can be implanted by tweezers and its cuff diameter can be adjusted through a self-locking structure including a plurality of ratchet teeth and a locking loop. This configuration has however several drawbacks: for instance, the teeth to secure the tie could be hazardous; the diameter of the cuff depends on the location of the ratchet teeth, and might not be perfectly adapted to the several sizes and shapes of the target nerve; once tighten, the cuff electrode cannot be reopened neither for size adjustment nor for explantation; of foremost importance, the Young's modulus of parylene is much higher than that of biological tissues, which can possibly engender, depending on the circumstances, mechanical mismatches between the implanted device and the target tissue bringing to possible inflammation and fibrotic scar development.

Similar to the above cuff electrodes, devices including fluidic/microfluidic channels or arrays have been described in the art, for instance by Cobo et al., (Journal of Microelectromechanical Systems, Vol: 28, Issue: 1, February 2019) reporting a Parylene C-based peripheral nerve interface that combines both electrodes and microfluidic channels. Again, as for the above parylene-based cuff electrode, the design and the materials used limit the usability of said cuff.

There is therefore a need to new configurations for cuff devices, such as cuff electrodes, which are safer, easily implantable and universal in design to be adapted ideally to any situation.

SUMMARY OF INVENTION

In order to address and overcome, or at least reduce, the above-mentioned drawbacks of the prior art solutions, the present inventors developed a new kind of cuff device having improved handling features and capabilities.

The invention provides a solution to overcome the drawbacks of the prior art such as those described in the previous chapter. According to one aspect of the present invention, the drawbacks of the background art concerning both the stability and the efficacy of nerves' interfaces are addressed and solved. A novel device is proposed that guarantee at the same time stimulation/sensing activity, mechanical stability with a nerve, and facility of implant.

The invention concerns interfaces for establishing electrical and/or fluidic contact with a living tissue, in particular it relates to a cuff device, such as a cuff electrode or a cuff with fluidic capabilities, for stimulation and/or sensing of a tubular body structure, such as a peripheral nerve, CNS nerve, gut structures, oesophagus etc., and to its use, e.g. within a neuro-prosthesis.

In particular, a first purpose of the invention was that of providing an easy to place, reversible solution for cuff devices, so to result more user-friendly in terms of manipulation.

Another purpose of the present invention was that of providing a universal design for a cuff device that could adapt to any tubular body structure size.

Still a further purpose of the present invention was that of providing a cuff device having optimized properties during surgical operations in a way not to compromise its mechanical properties and/or biocompatibility with bodily tissues of a subject upon application. All those aims have been accomplished with the present invention, as described herein and in the appended claims.

In particular, the invention feature a cuff device having an optimized combination of dimensions, materials and fixation system, leveraging the softness and stretchability to tighten the device around a tubular body structure. In one embodiment, the invention features a cuff electrode adapted to be fixed around a nerve. The device presents multiple advantages: it can be easily and rapidly fixated around a tubular body structure such as a nerve, it can easily adapt to the diameter of said tubular body structure and it works on various scales, so that it can be deployed around e.g. very small nerves (typically bellow 1 mm in diameter) up to around large structures such as around the gut (typically larger than 1 cm in diameter).

Moreover, the stretchability of the cuff device of the invention further solves the issue of keeping the pressure on a tubular body structure below certain thresholds without compromising the functionality and the compliance of the device; for instance, the pressure on a nerve shall stay below 20 mm Hg (the pressure at which venal blood flow inside the nerve starts to get disturbed with the potential effect of nerve damage).

Accordingly, in one aspect it is provided a cuff device as defined in claim 1.

According to a second aspect of the invention, it is provided system as defined in claim 10.

According to a further aspect of the invention it is provided a method as defined in claim 14.

Further embodiments of the present invention are defined by the appended claims.

The above and other objects, features and advantages of the herein presented subject-matter will become more apparent from a study of the following description with reference to the attached figures showing some preferred aspects of said subject-matter. However, the present invention is not limited to the embodiments as described in the following and/or depicted in the drawings; to the contrary, the scope of the present invention is defined by the appended claims.

DETAILED DESCRIPTION OF THE INVENTION

Figure 1:
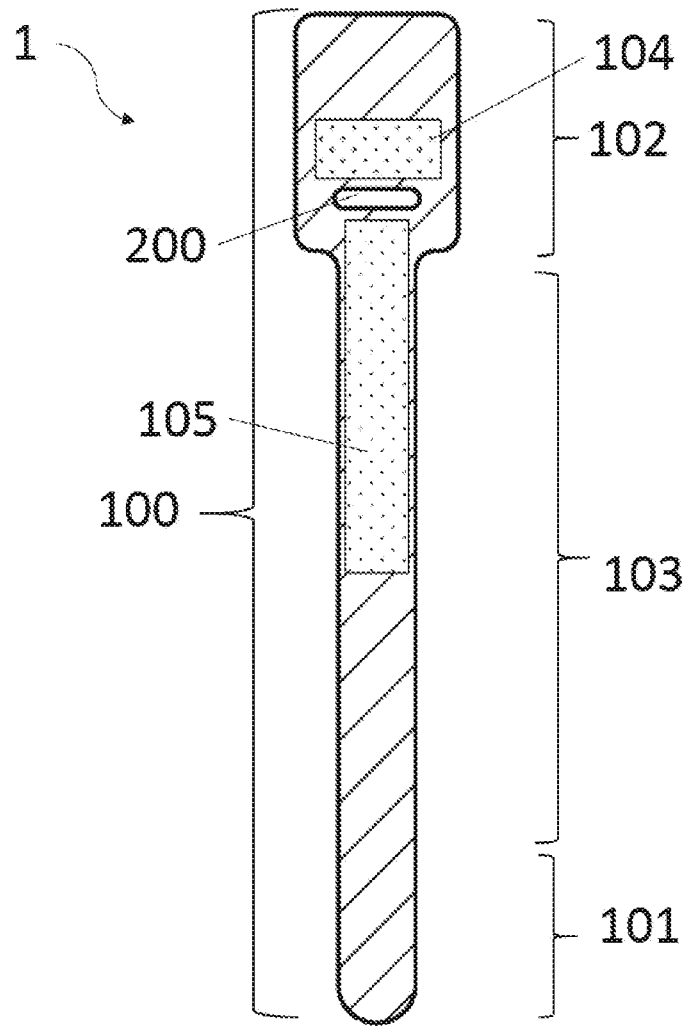
FIG. 1 depicts one embodiment of a cuff device according to the invention embodied as a cuff electrode having a single buckle.

The subject-matter herein described will be clarified in the following by means of the following description of those aspects which are depicted in the drawings. It is however to be understood that the subject matter described in this specification is not limited to the aspects described in the following and depicted in the drawings; to the contrary, the scope of the subject-matter herein described is defined by the claims. Moreover, it is to be understood that the specific conditions or parameters described and/or shown in the following are not limiting of the subject-matter herein described, and that the terminology used herein is for the purpose of describing particular aspects by way of example only and is not intended to be limiting.

Unless otherwise defined, technical and scientific terms used herein have the same meaning as commonly understood by one of ordinary skill in the art to which this invention belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated. Further, for the sake of clarity, the use of the term "about" is herein intended to encompass a variation of +/−10% of a given value.

The following description will be better understood by means of the following definitions.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

In the frame of the present disclosure, the expression "operatively connected" and similar reflects a functional relationship between the several components of the device or a system among them, that is, the term means that the components are correlated in a way to perform a designated function. The "designated function" can change depending on the different components involved in the connection; for instance, the designated function of electrodes operatively connected with connection means is to e.g. deliver electric current to a nerve in order to electrically stimulate it. A person skilled in the art would easily understand and figure out what are the designated functions of each and every component of the device or the system of the invention, as well as their correlations, on the basis of the present disclosure.

The expression "conductive track" refers to any film, path, stripe, strand, wire or the like which is electrically conductive in nature. For the sake of clarity, the word "electrode" is herein used to mean the distal part of a conductive track which is in direct contact with a subject's tissue. However, in embodiments of the invention, the term "electrode" is used to mean both a conductive track and its distal, terminal portion configured to interface with a biological tissue. Conductive tracks according to the present disclosure are used to connect and/or close an electrical circuit, and are thus usually electrical connectors or "interconnects". A conductive track is generally a metallic element that conducts an electric current toward or away from an electric circuit, but can be made of any suitable electrically conductive material, including but not limited to metals such as Au, Pt, Al, Cu and the like, as well as any alloy, oxides and/or combinations thereof; conductive polymeric materials; composite material such as polymeric materials embedding metal particles and/or metal strands or stripes, including insulating materials functionalized with electrically conductive flakes or fibers, for example carbon-filled polymers; liquid metals, including alloys or oxides thereof, such as gallium; electrically conductive inks; as well as any suitable combination thereof. Micro-lithography and/or micro-integrated electronics, among other techniques readily available in the art, can be adopted to fabricate the components of the electrodes.

The expressions "film" or "thin film" relate to the thin form factor of an element of the biomedical device of the invention such as a support substrate and/or a conductive track. Generally speaking, a "film" or "thin film" as used herein relates to a layer of a material having a thickness much smaller than the other dimensions, e.g. at least one fifth compared to the other dimensions. Typically, a film is a solid layer having an upper surface and a bottom surface, with any suitable shape, and a thickness generally in the order of nanometers, micrometers or even millimetres, depending on the needs and circumstances, e.g. the manufacturing steps used to produce it. In some embodiments, films according to the invention have a thickness comprised between 1 nm and 10 mm, such as between 1 nm and 10 nm, 20 nm and 100 nm, 5 µm and 5 mm, between 5 µm and 1 mm, between 10 µm and 1 mm, between 5 µm and 500 µm, between 50 µm and 500 µm between, between 50 µm and 150 µm, 100 µm and 500 µm or between 200 µm and 500 µm. When referring to thin electrode films, those can have a thickness comprised between 1 nm and 500 µm, such as between 20 nm and 200 nm or between 50 nm and 100 nm. These dimensions are considered to be optimal in the frame of the present invention for what concerns implantation maneuverability, stretchability and mechanical compliance of the device with the body tissues.

The term "subject" as used herein refers to mammals. For example, mammals contemplated by the present invention include human, primates, domesticated animals such as cattle, sheep, pigs, horses, laboratory rodents and the like.

As used herein, "treatment" and "treating" and the like generally mean obtaining a desired physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history, overweight status or age; (b) inhibiting the disease, i.e., arresting its development; or relieving the disease, i.e., causing regression of the disease and/or its symptoms or conditions such as improvement or remediation of damage. The term "diagnosis", "diagnostic" and the like refers to identifying the presence or nature of a pathological condition in a subject.

A "microfluidic device" is generally speaking any apparatus which is conceived to work with fluids at a micro/nanometer scale. Microfluidics is generally the science that deals with the flow of liquids inside channels of micrometer size. At least one dimension of the channel is of the order of a micrometer or tens of micrometers in order to consider it microfluidics. Microfluidics can be considered both as a science (study of the behavior of fluids in microchannels) and a technology (manufacturing of microfluidics devices for applications such as lab-on-a-chip). These technologies are based on the manipulation of liquid flow through microfabricated channels. Actuation of liquid flow is implemented either by external pressure sources, external mechanical pumps, integrated mechanical micropumps, hydrostatic pressures or by combinations of capillary forces and electrokinetic mechanisms. In the frame of the present invention, a microfluidic device can be easily adapted to work with fluid volumes spanning from milliliters down to femtoliters, and the dimensions can be adapted accordingly to have channels within the millimeter scale.

The present invention features a cuff device comprising:
a) a support having a first end, a second end and an elongated body in between;
b) connection means for electrical, magnetic and/or fluidic connection with external devices;
c) at least one of
i) an electrode and/or an electronic component operatively connected with said connection means configured to electrically interface with a biological tissue and
ii) a channel having an inlet, an outlet and an elongated body in between operatively connected with said connection means via said inlet and configured to fluidically interface with a biological tissue via said outlet; and
d) at least one buckle configured to receive said first end and permit the sliding therein of said elongated body so to close and lock the cuff electrode at desired positions
characterized in that said support is stretchable.

In one embodiment, the cuff comprises an array of electrodes, which are preferably stretchable. In an alternative or additional embodiment, the cuff comprises an array of microfluidic channels.

With reference to FIG. 1 depicting one embodiment of the invention, a cuff electrode 1 is shown comprising:
a) a support 100 having a first end 101, a second end 102 and an elongated body 103 in between;
b) connection means 104 for electrical and/or magnetic connection with external devices;

c) at least one electrode and/or electronic component 105 operatively connected with said connection means 104 configured to interface with a biological tissue; and d) at least one buckle 200 configured to receive said first end 101 and permit the sliding therein of said elongated body 103 so to close and lock the cuff electrode at desired positions characterized in that said support 100 is stretchable.

The stretchability of the support 100 is provided by the materials this is substantially composed of. In this context, in preferred embodiments the support substrate 100 is substantially made of a soft polymeric material, or combinations of many soft polymeric materials, particularly biocompatible ones, or polymeric materials coated with soft polymeric material or hydrogels, or made of composite materials. Preferred soft materials are elastomeric materials, thermoplastic elastomers (a class of copolymers or a physical mix of polymers, usually a plastic and a rubber, which consist of materials with both thermoplastic and elastomeric properties), foams, gels or hydrogels. As a way of example, the substrate 100 can be substantially composed of one or more polymer selected from a non-exhaustive and non-limiting list comprising thermoset materials such as alkyds, epoxies, polyester thermosets, unsaturated polyesters, polyurethane, bis-maleimides (BMI), silicone materials such as polydimethylsiloxane (PDMS) or other medical grade silicones and any combination thereof; nitrile rubber, latex, hydrogels such as polyhydroxymethylacrylate and its derivatives, poly(lactic-co-glycolic acid), lactide and glycolide polymers, caprolactone polymers, polyisoprene (synthetic rubber), polyurethane foam (foam rubber), XPS foam, styrenic block copolymers, elastomeric alloys, hydroxybutyric acid, polyanhydrides, polyesters, polyphosphazenes, polyphosphoesters and poly(glycerol sebacate acrylate), polypropylene, polypropyleneoxide or their derivatives, polymethylenoxide or its derivatives, polyethylene or its derivatives such as polyethylene glycole (PEG), polyethylenoxide or their derivatives, polyacrylate or its derivatives, poly(vinyl alcohol) (PVA), poly(lactic acid), poly(methacrylic acid), and copolymers, poly(vinylpyrrolidone) (PVP) and combinations thereof; as well as any combination of the foregoing. These materials can be mixed with particle such as carbon nanotube, gold particles, platinum particles or diamond particle or any combinations such as to improve mechanical, electrical or thermal properties.

Still preferably, the support 100 is reversibly stretchable (elastic). In particular, support 100 can withstand an elongation or multidirectional strain, upon a single or multiple cycles, comprised between 1 and 500%, preferably at least 5%, such as about 50%, about 100% or about 200%, of its size at rest without cracking or loss of its mechanical properties, which represents an advantage in those clinical contexts and/or body structures in which several cycles of mechanical stresses over time can be foreseen. Further, the support 100 has a Young's modulus comprised between about 1 kPa and 1 GPa, such as for instance between about 100 kPa to about 1 GPa, between about 100 kPa to about 1 GPa, between about 5 MPa to about 1 GPa, between about 100 kPa to about 100 MPa, between about 100 kPa to about 5 MPa, between about 10 kPa to about 300 kPa or between about 10 kPa to about 10 MPa, preferably between about 1 MPa to about 10 MPa, which are suitable ranges of values matching the Young's modulus of many biological tissues and surfaces to avoid mechanical mismatches between said tissues and a biomedical device, and/or for mimicking physical and/or mechanical properties of bodily tissues. In the frame of the present invention, "physical and/or mechanical properties" means, by way of examples, stress-strain behaviour, elastic modulus, fracture strain, conformability to curvilinear surfaces, thickness, area and shape which have to be as similar as possible to those to be found in tissues of a subject's body.

In a most preferred embodiment, the support 100 is an elastomeric substrate, for instance a PDMS substrate. The support 100 can be implemented as a thin film substrate, having a flat appearance and a thickness comprised between about 1 μm and about 5 mm, such as between about 5 μm and about 5 mm, between about 5 μm and about 1 mm, between about 10 μm and about 1 mm, between about 5 μm and about 500 μm, between about 50 μm and about 500 μm, between about 50 μm and about 150 μm, between about 100 μm and about 500 μm or between about 200 μm and about 500 μm. A PDMS substrate having the above thickness and form factor presents several advantages in the frame of medical devices according to the invention, such as biocompatibility, mechanical compliance with regards to body tissue, possibility to be sterilized and high stretchability.

In embodiments of the cuff device envisaging a cuff electrode and/or electronic components, as the ones depicted for instance in FIGS. 1 to 6, said cuff device features connection means 104 for electrical and/or magnetic connection with external devices. Connection means 104 can be implemented for instance as electrical pad(s) for establishing an electrical connection between electrodes interconnects and/or electronic component 105 and one or more electrical and/or electronic device 300 (see for instance FIG. 5) via wired connections; additionally or alternatively, connection means 104 can be implemented as wireless means for coupling the cuff electrode of the invention with external receivers in a wireless mode, for instance through (resonant) inductive coupling, (resonant) capacitive coupling, magnetodynamic coupling, ultrasounds and/or infrared radiation, by the simple implementation of solenoid antennas or coils in any suitable position within the device. Accordingly, the connection can be operatively established in any suitable way; with reference for instance to the embodiment shown in FIG. 5, a connection wire 301 runs from an electrical and/or electronic device 300 towards a connection pad 104.

Figure 7:
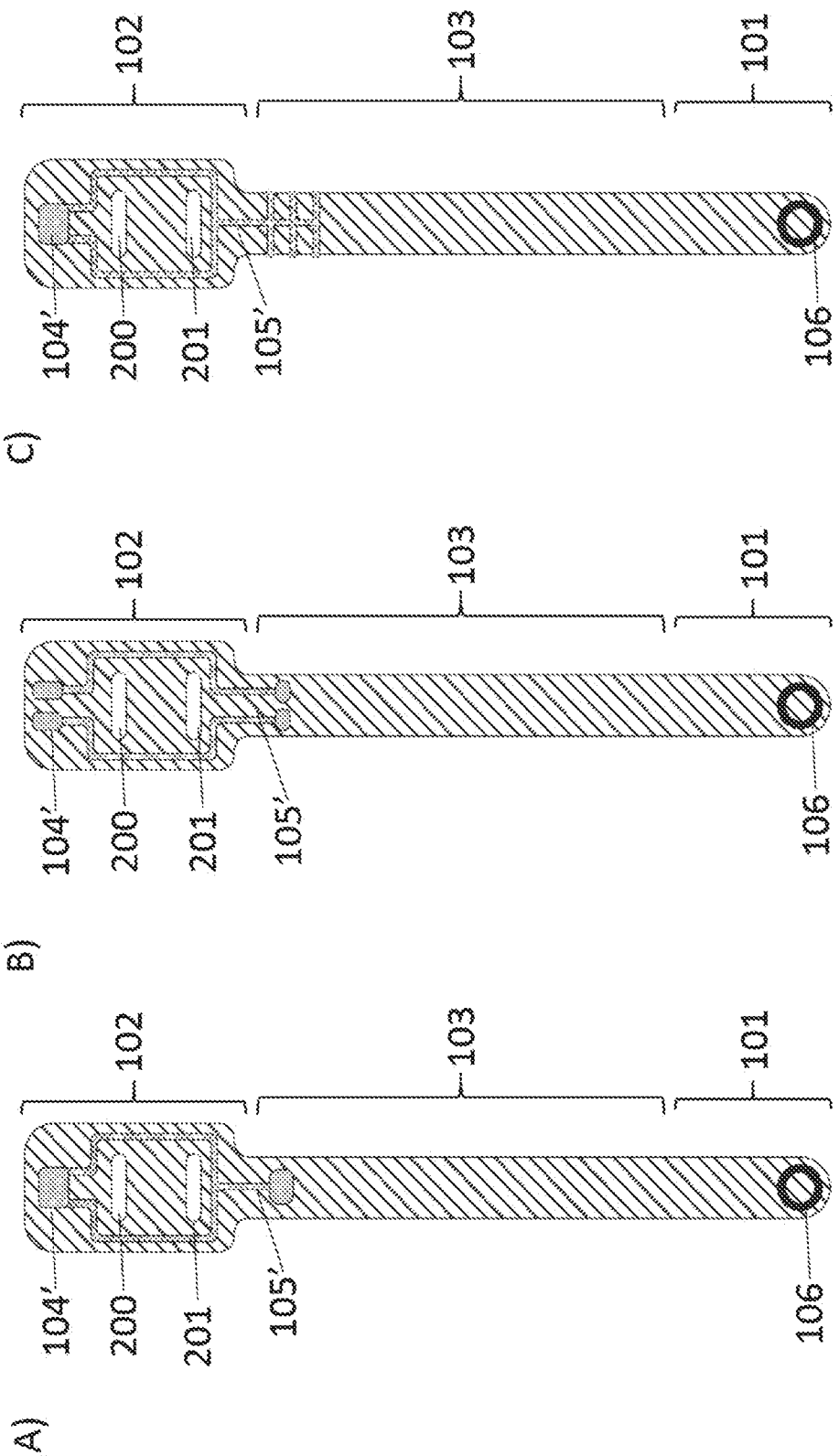
FIG. 7 depicts three embodiments of a cuff device according to the invention embodied as a microfluidic cuff device having two buckles: A) embodiment comprising one fluidic connection means and one outlet connected via a branched microfluidic channel; B) embodiment comprising two fluidic connection means and two outlets connected via two microfluidic channels; C) embodiment comprising one fluidic connection means and a plurality of microfluidic channels and outlets.
Figure 8:
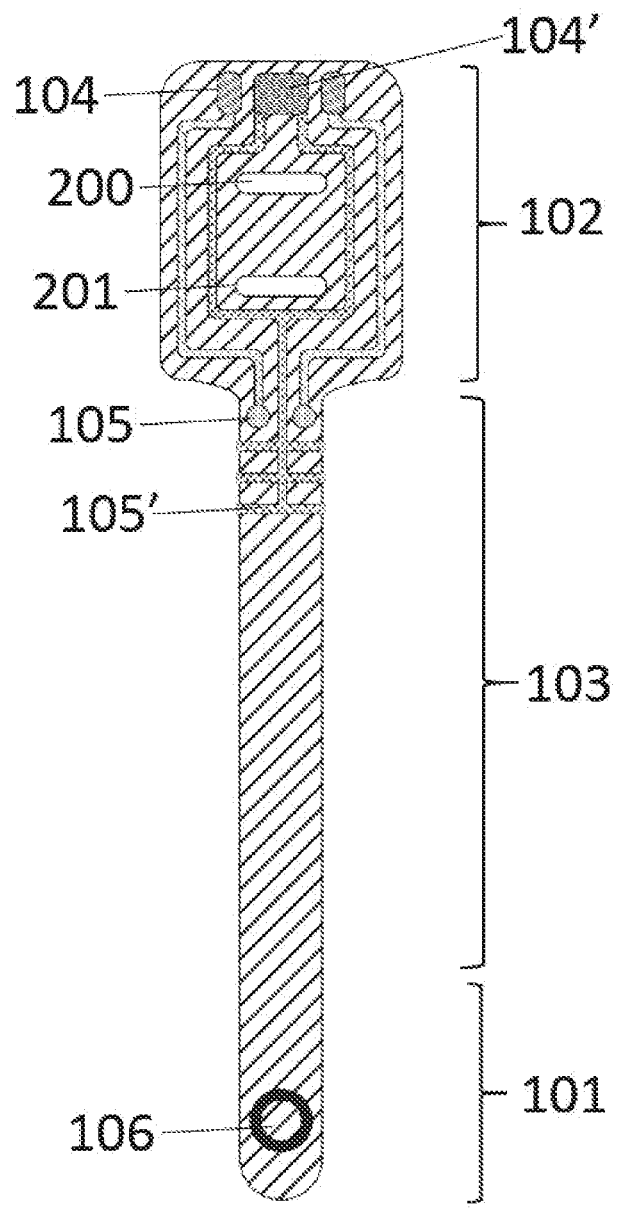
FIG. 8 depicts one embodiment of a cuff device according to the invention embodied as a "hybrid" electrical/microfluidic cuff device, comprising two buckles, connection means for both electrical and fluidic connection with external devices, and several electrodes and fluidic channels operatively connected with connection means.

With reference to FIG. 7, alternative or additional embodiments of the invention are shown in which connection means 104' are included into a cuff device, and which are configured for fluidic connection with external devices. Fluidic connection means 104' can be implemented for instance as mL, μL or nL-scale reservoirs, tubes and/or channels embedded into, located onto or otherwise connected to, the support 100 in any suitable way as known in the art such as gluing, molding, scissor blading, (photo) lithography, etching, screen printing, riveting and the like. Connection means 104' can be implemented for instance as mL or μL-scale reservoirs and/or tubes for establishing a fluidic connection between channels 105' and one or more external device 300' such as syringes, external mechanical pumps, integrated mechanical micropumps, peristaltic pumps, haemostatic pumps and the like.

In embodiments of the cuff device envisaging a cuff electrode, the support 100 comprises at least one electrode and/or electronic component 105 operatively connected with said electrical connection means 104, and configured to interface with a biological tissue. Typically, in one set of embodiments, electrode and/or electronic component 105 comprise one or more conductive tracks, acting as interconnects between a subject's tissue and the connection means 104. Electrode and/or electronic component 105 preferably comprises a distal, end electrode portion, such as a pad, configured to directly interface a bodily tissue either directly or through an electronic component. Conductive tracks and/or electrode pads of the electrode and/or electronic component 105 can be made of any suitable electrical conductive material, including but not limited to metals such as Au, Pt, Al, Cu, Pt—Ir, Ir, and the like, as well as any alloy thereof, oxide thereof and combinations thereof, composite metal-polymer materials, such as Pt-PDMS composites or Pt—Ir-PDMS composites or Ir-PDMS composites and so forth, as well as conductive polymers such as poly(3,4-ethylenedioxythiophene) polystyrene sulfonate (PEDOT: PSS) or polypyrrole (PPy). In a preferred embodiment, the electrodes are made of non-toxic and biocompatible materials. Electrode and/or electronic component 105 or portions thereof (e.g. conductive tracks or electrode pads) can be placed on or within the support 100 with any suitable means such as for instance photolithography, electron beam evaporation, thermal evaporation, sputter deposition, chemical vapour deposition (CVD), electro-plating, molecular beam epitaxy (MBE), inkjet printing, stencil printing, contact printing, transfer printing or any other conventional means known in the art. In embodiments, conductive tracks are encapsulated later on, preferably with the soft stretchable material comprised in the support 100, to avoid short circuits and failure thereof, i.e. passivated whilst leaving the electrode pads exposed through connecting vias.

In a set of embodiments according to the invention, the at least one electrode 105 is a compliant electrode. A "compliant electrode" is any structure or element able to deliver an electric current, and adapted to change its shape according to the shape change of the support it adheres to, without substantially compromising mechanical and/or electrical performances. The term "compliant" is intended to include any conformable structure which is compressible, reversibly compressible, elastic, flexible, stretchable or any combination thereof. Examples of compliant electrodes known in the art include metal thin-films (including patterned electrodes, out-of-plane buckled electrodes, and corrugated membranes), metal-polymer nano-composites, carbon powder, carbon grease, conductive rubbers or conductive paints, a review of which is provided in Rosset and Shea (Applied Physics A, February 2013, Volume 110, Issue 2, 281-307), incorporated herein in its entirety by reference. As it will be apparent to those skilled in the art, built-in multilayers or stacks of several layers of any of the above polymeric, composite, metallic and/or oxide materials, as well as combinations thereof, are encompassed in the definition of compliant interconnect. Preferably, the electrodes are stretchable electrodes. In some embodiments, stretchable electrodes as the ones described in International Patent Applications WO 2004/095536, WO 2016/110564 and/or WO 2018/100005A1, incorporated herein in their entirety by reference, can be used.

In one set of embodiments, the cuff electrode of the invention comprises one or more arrays of elastically stretchable microelectrodes 105. As used herein, for the sake of clarity and conciseness, a "stretchable microelectrode array" refers to the ensemble of a plurality of electrodes 105 having the ability to withstand mechanical deformations such as flexing, stretching, torsion or the like, without electrical failure or loss of their electrical features. Stretchable arrays (for instance stretchable gold and/or Cr/Au and or stretchable platinum and/or Ti/Pt microelectrode arrays, MEAs) are becoming more and more popular and find convenient applications in the field of wearable electrodes, and/or implantable neuroprosthetic interface applications, and/or as electrode arrays for cell culture and tissue slice culture, and/or even for sensing robotic skins or the like. Accordingly, microelectrode arrays are particularly suitable to be used as a neural interface with the spinal cord, brain or peripheral nerves or soft biological tissue, for instance for the purpose of stimulating and/or recording a neurological or otherwise electrical activity e.g. in a nerve.

It has in fact been verified that microelectrode arrays, even upon deformation and after repeated torsions, keep their performances, thereby facilitating the recording of small amplitude biological signals and ensuring efficient functional electrical stimulation, as well as no or little degradation of the implant even after several months from implantation. Three exemplary embodiments of a cuff electrode of the invention featuring a microelectrode array are shown in FIG. 4A)-C).

In embodiments of the invention, as the one exemplarily depicted in FIG. 7, the cuff device comprises at least one channel 105' such as a microfluidic channel, configured to transport a fluid, rendering de facto the cuff device of the invention a fluidic or microfluidic device, depending on the needs and circumstances. In some embodiments, the cuff device comprises a plurality, such as an array, of channels or microchannels 105'. Preferably, fluidic or microfluidic channels according to the invention are embedded in the conformable substrate 100. Those fluidic channels 105' may be used for instance to supply a compound, such as a pharmaceutical compound, a gas, a buffer medium and the like, to the implantation site in order to maintain fluid circulation and thermo-regulation, and/or for pharmacologically stimulating a body tissue. The fluidic channels 105' of the device according to the invention can be used e.g. for delivering drugs such as dopamine, serotonin or others, to remove locally generated heat or unfavourable electrochemical products or waste products, or even to deliver surgical adhesives for fixation purposes. For this, a connection of at least some of the fluidic channels 105' to the outside can be provided, if the device is fully implanted, via the above mentioned fluidic connection means 104'. Additionally or alternatively, the channels 105' can be operatively connected through their inlets to a fluidic pump or some other drug delivery device 300', via fluidic connection means 104'.

As exemplarily depicted in FIG. 1, showing a cuff device embodied as a cuff electrode as a way of non-limiting example, the cuff electrode comprises a body 100 having a first end 101, a second end 102 and an elongated body 103 in between. In embodiments of the invention, at least said elongated body 103 has a flat appearance; in additional or alternative embodiments of the invention, said first end 101 has a flat appearance as well; in additional or alternative embodiments of the invention, said second end 102 has also a flat appearance. In preferred embodiments, the entirety of the support 100 has a flat appearance. In the embodiment depicted in FIG. 1, the cuff electrode comprises one buckle 200 configured to allow said first end 101 to enter and permit the sliding of the elongated body 103. In operation, once the cuff electrode is placed around a nerve, the first end 101 is slid through the buckle 200 and the elongated body 103 starts wrapping around said nerve in a way to close and lock the cuff electrode at desired positions. The thickness, Young's modulus and elasticity of the implant plays a crucial role in how well the mechanism behaves. With materials too stiff and not elastic, such as those taught in the art like polyimide or parylene, the system will not stay closed without additional elements such as ratchet teeth. To the contrary, the use of a stretchable material such as elastomeric polymers for producing the support 100 plays an important role in the frame of the invention, also because of the intrinsic stickiness and shear friction occurring between the internal sides of the buckle 200 and the body 103 of the cuff electrode upon relative contact.

Material wise, the Young's modulus of bodily tissues, such as tubular structures or nerves, is generally speaking in the range of 1 to 10 MPa; therefore, the use of a soft material as the ones proposed herein is ideal, also because of the possibility to secure the cuff without any rigid or sharp parts, thus avoiding or at least reducing the risk of damaging the nerve. The use of a soft and stretchable material such as an elastomeric polymer has the additional advantage that can be easily cut and removed depending on the needs and circumstances. For instance, the first end 101 and possibly part of the elongated body 103, upon placement of the cuff around a target nerve, can be e.g. scissor cut to remove surplus portions no more needed or useful functionally. As a result, a smaller, less invasive and better tolerated implant can be obtainable with a cuff electrode according to the invention.

Figure 2:
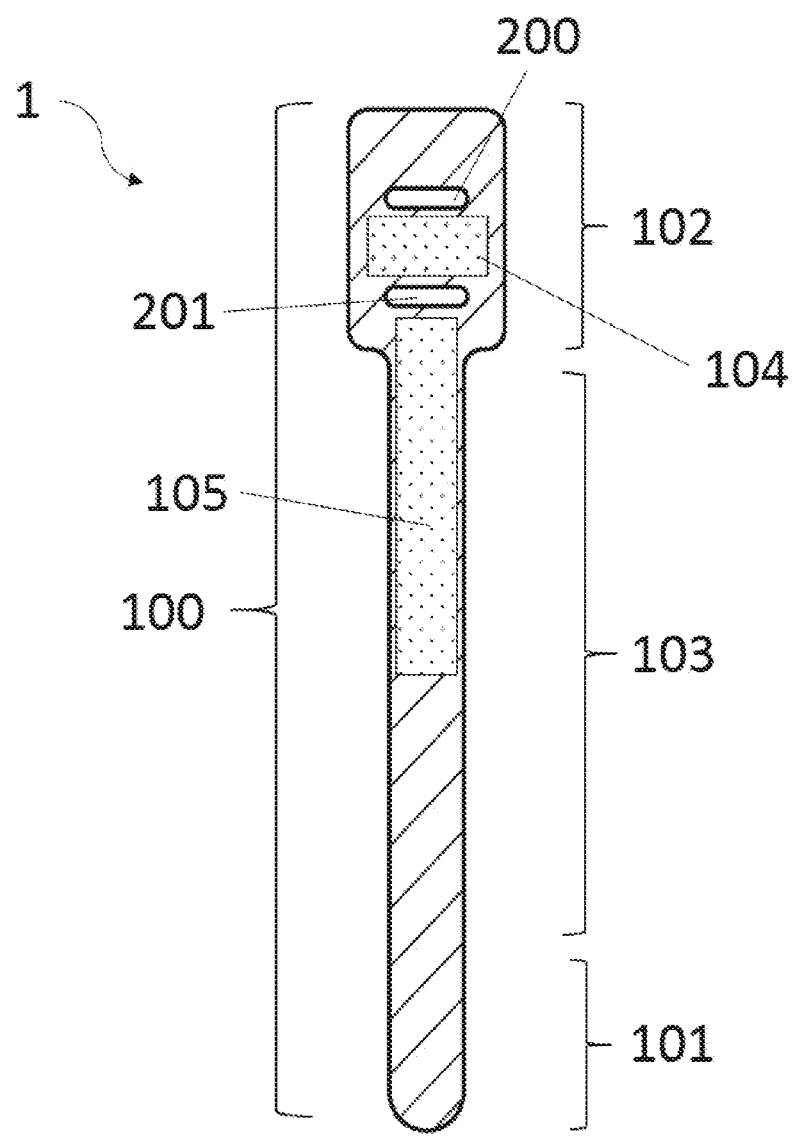
FIG. 2 depicts one embodiment of a cuff device according to the invention embodied as a cuff electrode having two buckle.
Figure 3:
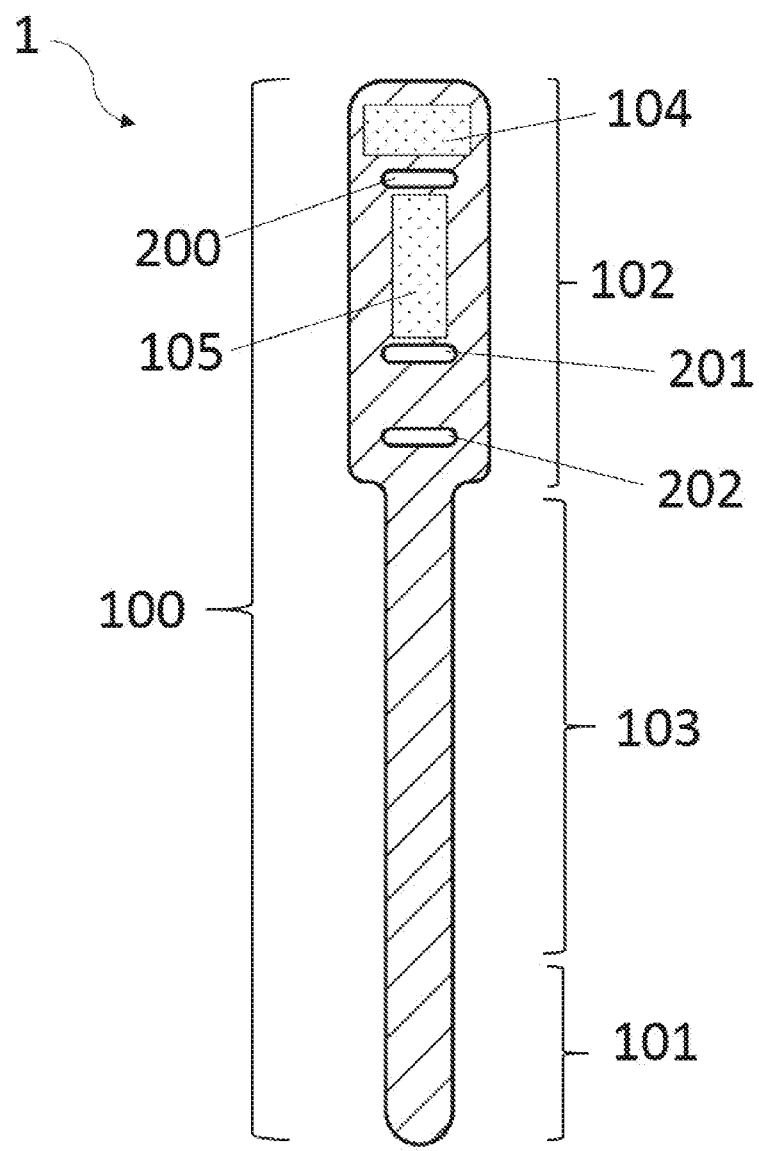
FIG. 3 depicts one embodiment of a cuff device according to the invention embodied as a cuff electrode having three buckles.
Figure 4:
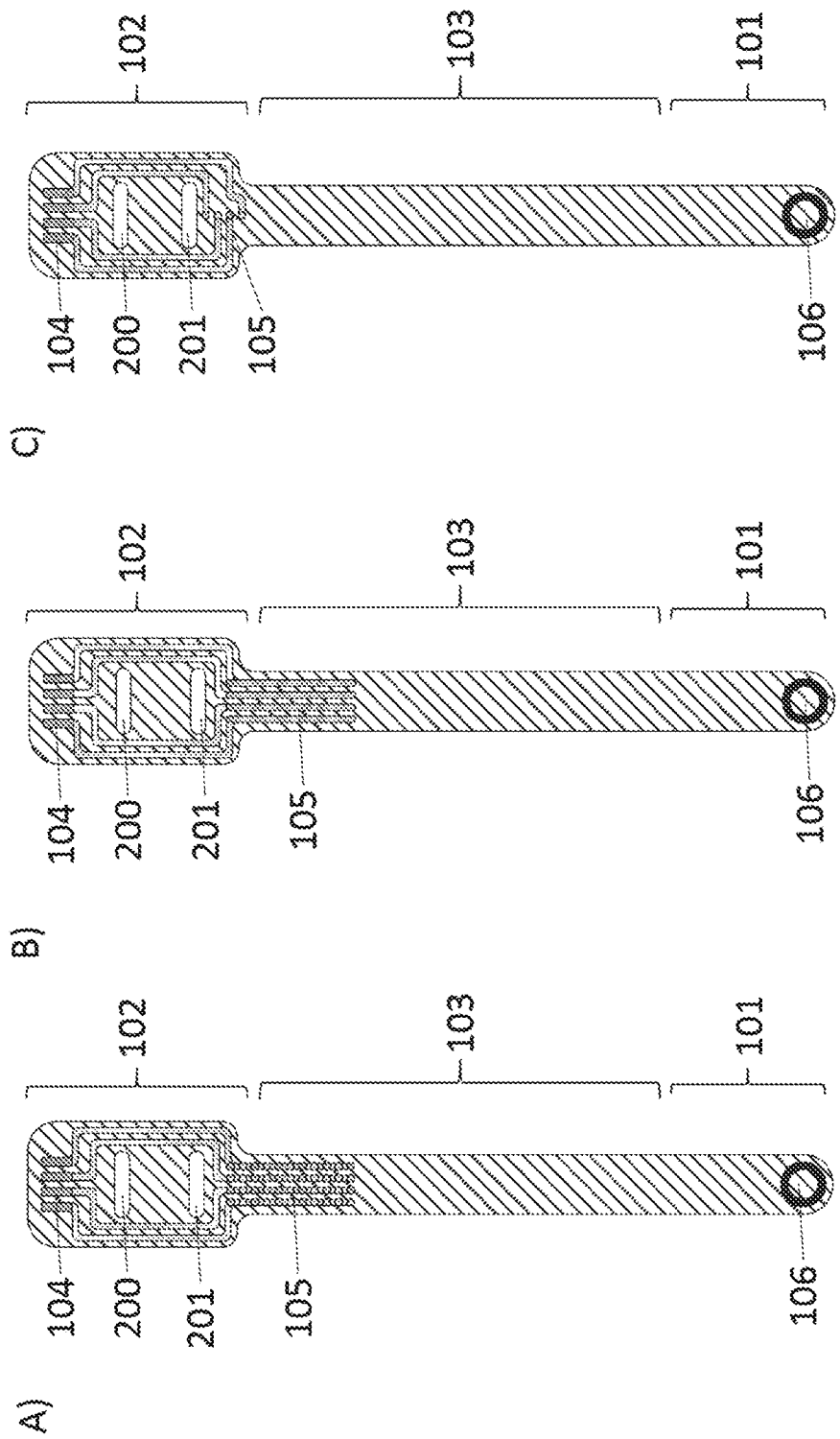
FIG. 4 depicts three embodiments of a cuff device according to the invention embodied as a cuff electrode having a microelectrode array and two buckles: A) multi-spots electrode array having electrical spots located on the elongated body of the device; B) microelectrode array having elongated electrodes placed on the elongated body of the device; C) multi-spots electrode array having electrical spots located on the second end of the device.

As shown for instance in FIGS. 1 to 3 and FIG. 8, in embodiments of the invention the second end 102 of the support 100 has a larger surface compared to the rest of the support, in order to more easily accommodate buckles 200 and/or additional components such as connection means 104, 104' and/or electrodes 105/channels 105' outlets. A plurality of alternative or combined embodiments can be envisaged depending on the configurations, sizes, positioning etc. of the various elements of the cuff electrode of the invention on/in the first end 101, second end 102 or elongated body, alone or in combination. For instance, said at least one electrode 105/channel 105' outlets can be located on said second end 102 (see for instance FIGS. 3 and 4C) and/or on said elongated body 103 (see for instance FIGS. 1, 2, 4A and 4B). Preferably, said at least one buckle 200 is located on said second end 102, and advantageously the cuff device can comprises at least two or at least three buckles 200-202 (see for instance FIGS. 2, 3 and 4A-C). In exemplary embodiments, the cuff device of the invention comprises two (see for instance FIG. 6A) or more, such as three, buckles (see for instance FIG. 6B) that allow to easily secure the electrode around the tubular structure 400 without any rigid part. This system also allows adjustment (of diameter) during surgery, thanks to multiple electrodes/channels sites insuring that electrodes 105 and/or channels 105' outlets are in contact with a tubular structure 400 of a subject no matter the size of said structure. In a preferred embodiment, the cuff device of the invention comprises two buckles 200, 201, electrode element(s) 105 and/or channel 105' outlet(s) along the elongated body 103 and connections means 104, 104' on the second end 102, between said buckles 200, 201 (FIGS. 2 and 6A). This configuration facilitates at the same time the fixation of the cuff around a tubular structure, such as around a nerve, a good electrical/fluidic contact between the tubular structure/nerve 400 and the cuff as well as the functional, such as electrical, contact between the connection means 104, 104' and external devices 300, 300'. In another preferred embodiment, the cuff device, such as a cuff electrode according to the invention, comprises three buckles 200-202, with electrode element(s) 105 and/or channel 105' outlet(s) located between two buckles 200, 201 on the second end 102. This configuration allows less lost space and better coverage of the tubular structure, e.g. a nerve (FIGS. 3 and 6B).

Optionally, said at least one electrode 105 and/or channel 105' outlet is located on said second end 102, and in between at least two buckles 200, 201 (see for instance FIG. 3). Advantageously, in sets of embodiments, said connection means 104, 104' can be located on said second end 102 (see for instance FIGS. 1, 2, 3 and 4A-C).

In some embodiments, as shown in FIGS. 4A-C and FIGS. 7 to 9, the cuff device comprises at least one reinforcement structure 106 located on said first end 101. The reinforcement structure can be embodied as e.g. a ring made of a stiffer material such as a biocompatible polymer or plastic. The reinforcement structure 106 is meant for a user such as a surgeon to pass a suture wire through and help fasten the cuff by using the suture wire as a guide to let the first end 101 pass through the buckle(s). The reinforcement ring 106 prohibits the implant to tear if a needle is passed through it. After the implant has been fastened around a nerve or other tubular biological structures, the excess of the strip of the first end 101 can be easily cut away, thanks to the soft nature of the support 100, also removing the reinforcement ring 106 and thus leaving only soft material in the body.

Figure 11:
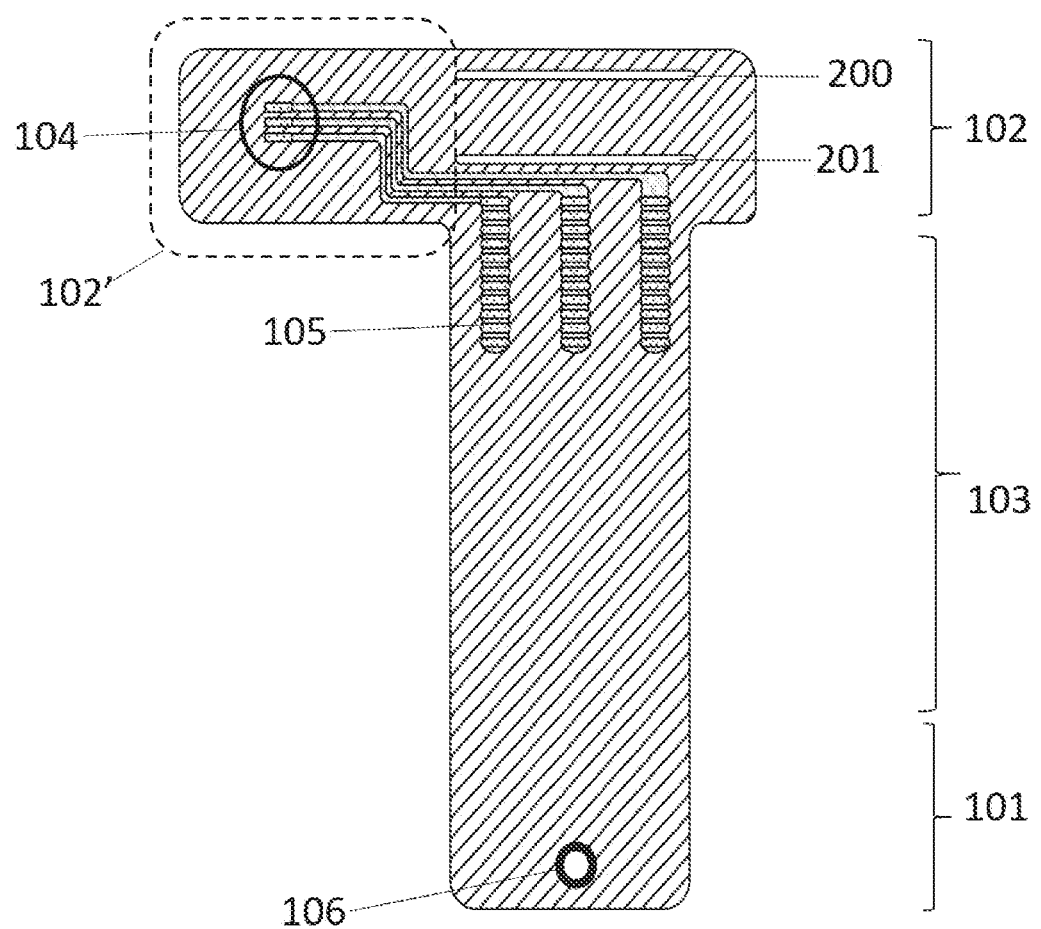
FIG. 11 depicts an embodiment of a cuff device according to the invention embodied as a "L shape" cuff electrode having a microelectrode array and two buckles, comprising an individually addressable multi-spots electrode array having electrical spots located on the elongated body of the device and means for electrical and/or magnetic connection with external devices located on a lateral portion of the second end.

In still another embodiment, as shown in FIG. 11, the cuff device according to the invention is embodied as an "L shape" cuff electrode in which the second end 102 comprises a lateral, elongated portion 102' perpendicular to the elongated body 103, and the connection means 104, 104' are located on said lateral, elongated portion. In the shown, non-limiting embodiment, the cuff device comprises a microelectrode array 105 and two buckles 200, 201, the microelectrode array 105 comprising an individually addressable multi-spots electrode array having electrical spots located on the elongated body 103 of the device and means 104 for electrical and/or magnetic connection with external devices located on a lateral, elongated portion 102' of the second end 102. This embodiment advantageously allows to limit the mechanical stress with the tubular body structure of a subject, such as a nerve, by permitting the gather means 104 and electrical tracks or paths on said lateral elongated portion 102' of the second end 102 to run along the nerve length, thus also facilitating implant and fixation operations.

The cuff device of the invention is intended to be in one embodiment as a peripheral or Central Nervous System (CNS) nerve interface, acting as a bridge between the peripheral/central nervous system and external devices to bi-directionally transducing recorded information and/or sending signals between the human body and a machine processor, and particularly as a fixed or removable implant configured to interface with a nerve with the purpose of electrically sensing and/or stimulating an electrical activity in a subject.

Accordingly, the cuff electrode can be configured as a way of example as a fixed or removable neural or nerve implant, heart implant, kidney implant, pancreatic implant, bladder implant, retina implant or gut implant, to mention some. Within the meaning of the present invention, a "fixed implant" defines a biomedical device having the ability to conform to established and/or customised surgical procedures and to reside in vivo without producing adverse biological reactions over extended periods of time, such as for instance over 7 days. Still within the meaning of the present invention, a "removable implant" defines a biomedical device having the ability to conform to established and/or customised surgical procedures and to reside in vivo for a limited amount of time, such as for instance the time of a surgical operation.

In additional or alternative embodiments, the cuff device is intended and configured to be used as a wrapping interface for tubular bodily structures such as a gut structure, oesophagus, urethra, ureter, arteries, to cite some.

Figure 5:
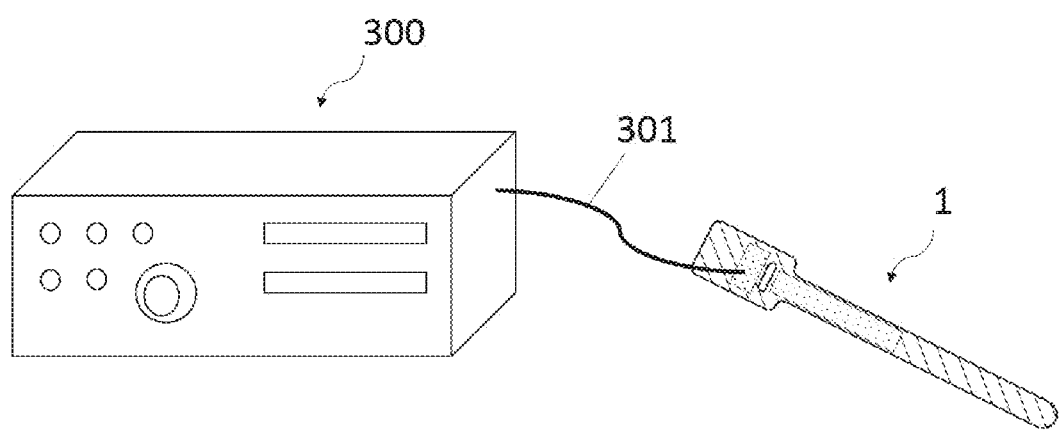
FIG. 5 depicts one embodiment of a system comprising a cuff device according to the invention embodied as a cuff electrode having a single buckle operatively connected to an external device such as an electrostimulator via electrical connection means.
Figure 6:
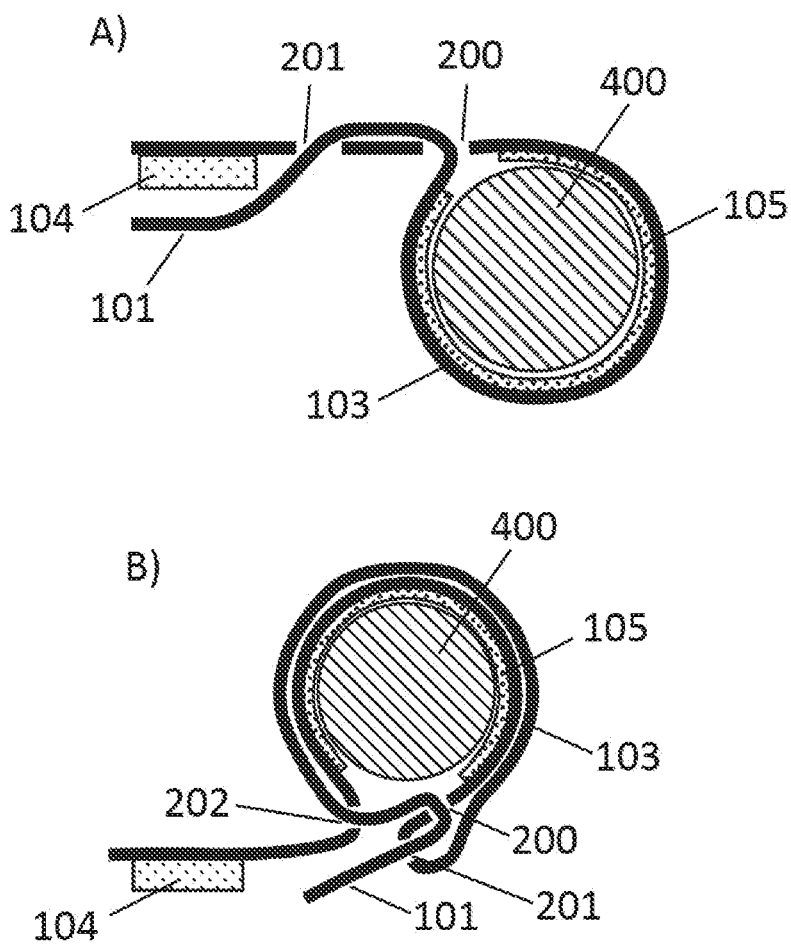
FIG. 6 depicts two embodiments of fasten mechanism of the device around a tubular body structure: A) exemplary fasten mechanism for a device having two buckles; B) exemplary fasten mechanism for a device having three buckles.

As briefly anticipated elsewhere, in one aspect the invention pertains to a system comprising the cuff device as described herein operatively connected with an external device 300, 300' through the connection means 104, 104'. For instance, the system can comprise a cuff electrode as described herein operatively connected with an external device 300 through the connection means 104 (FIG. 5). In embodiments of the invention, said external device 300, 300' might be selected from a list comprising an electro-stimulator, an electrical amplification and recording system, a telemetric device, a syringe pump, a pressure based pumping system, a haemostatic pumping system or combinations thereof. The external device 300, 300' can operate in closed-loop or open-loop mode with the cuff device, such as cuff electrode, of the invention. The described system can be used e.g. for treating, diagnosing, monitoring and/or preventing signs and/or symptoms associated to pathological conditions.

In view of what said above up to now, it would be evident for a person skilled in the art that in certain embodiments the cuff electrode of the invention can be used for electrically sensing a physiological parameter or stimulating an electrical response in a nerve of a subject. The sensing or stimulation activity can be performed in the frame of a therapeutic or preventive (e.g. for diagnostic purposes) medical treatment in a subject. Accordingly, a further aspect of the invention concerns the use of a cuff device, such as a cuff electrode, or of a system according to the present disclosure for sensing a physiological signal and/or stimulating an electrical activity and/or pharmacological activity of a tubular body structure, such as a nerve, of a subject. Advantageously, the use of the cuff electrode or of the system can be intended for treating one or more pathological conditions.

For instance, the device, system and methods according to the present disclosure can be used in a variety of situations for treating one or more pathological conditions wherein sensing and/or stimulating a nerve or other bodily tubular structures might be beneficial, and in many applications related to peripheral nerve pathological conditions including sensory feedback and/or motor feedback. A non limiting, exemplary list of uses of the cuff device as well as a system according to the present invention comprises treatment of foot drop, treatment of bladder incontinence, treatment of obstructive sleep apnea, treatment of diabetes by hepatic vagus nerve stimulation, treatment of erectile disfunctions, phrenic nerve stimulation, treatment of intractable epilepsy or treatment-resistant depression by Vagus nerve stimulation (VNS), sensory feedback and/or control with prosthetic limbs and facial nerve stimulation and recording for the treatment of ischemic stroke or for recovery of facial expressions. Cuff electrodes can also be used for the stimulation of other tubular structures in the body such as for intestinal track stimulation for treatment against constipation or stomach stimulation for the treatment of eating disorders.

When in use, the electrodes 105 are electrically connected through conductors 300 to an external device 400 for delivering an electrical current and/or for biological signal sensing, such as a neuromuscular electrical stimulator or a biological signal acquisition system (e.g. that can acquire for example electromyography—EMG—signals), depending on the application of interest.

For instance, in an embodiment of the invention, the external device 300 can be a portable neurostimulator wired via the connection means 104 to the electrodes 105 that are implanted around a nerve such as the sciatic nerve. The nerve stimulation can be wired or wirelessly driven e.g. by a controller external to the body, transducing the readout of a sole sensor fitted into a shoe under the foot into stimulation parameters. This arrangement, restoring sensory feedback from the foot sole, enables diabetic people to correctly walk and to cure ulcers, avoiding amputation. Indeed, the main cause of foot ulcers is abnormal gait due to loss of sensitivity under the foot sole, caused by the degeneration of the nerve endings located in the foot. The same teaching is applied, mutatis mutandis, to other external devices 300' operatively coupled with connection means 10'4 to microchannels 105' whose outlets contact a bodily tubular structure.

As it will be evident to a person skilled in the art, in one aspect the invention features a method for sensing a physiological signal and/or stimulating an electrical and/or pharmacological activity in a tubular body structure of a subject comprising the steps of:

a) providing a system as described herein;
b) inserting the first end 101 of the cuff device into the at least one buckle 200 in a way to wrap the cuff device around a tubular body structure 400 of said subject; and
c) sliding the elongated body 103 within said at least one buckle 200 so to close and lock the cuff device in a position permitting said tubular body structure 400 to be contacted by at least one electrode and/or channel 105, 105' outlet of said cuff device.

In one embodiment, said method comprises the steps of:
a) providing a system according to the present invention;
b) inserting the first end 101 of the cuff electrode of the invention into the at least one buckle 200 in a way to wrap around a nerve 400 of a subject; and
c) sliding the elongated body 103 within said at least one buckle 200 so to close and lock the cuff electrode in a position permitting said nerve 400 to be contacted by at least one electrode 105 of said cuff electrode. Two embodiments of the method of the invention are exemplarily shown in FIGS. 6A) and B). Additionally, the method can comprise a step of operating the external device 300, 300' of the system of the invention in a way as to sense and/or stimulating an electrical or pharmacological activity in a tubular bodily structure 400, such as a nerve, of a subject, such an activity being for instance an action potential in a nerve.

Figure 9:
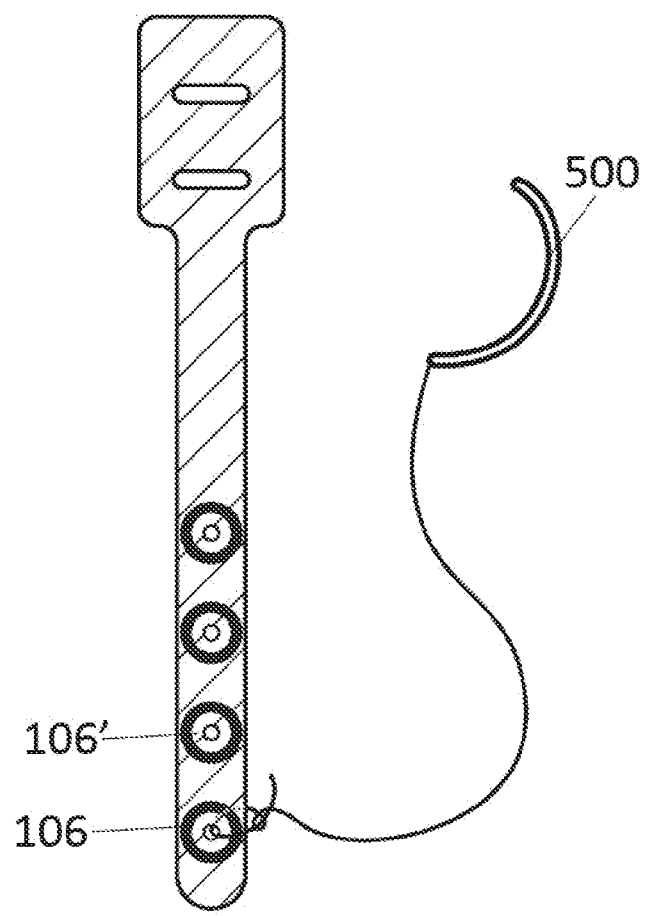
FIG. 9 depicts an exemplary device according to the invention having a plurality of reinforced rings for manipulation with surgical tools, such as surgical threads and blunt needles.
Figure 10:
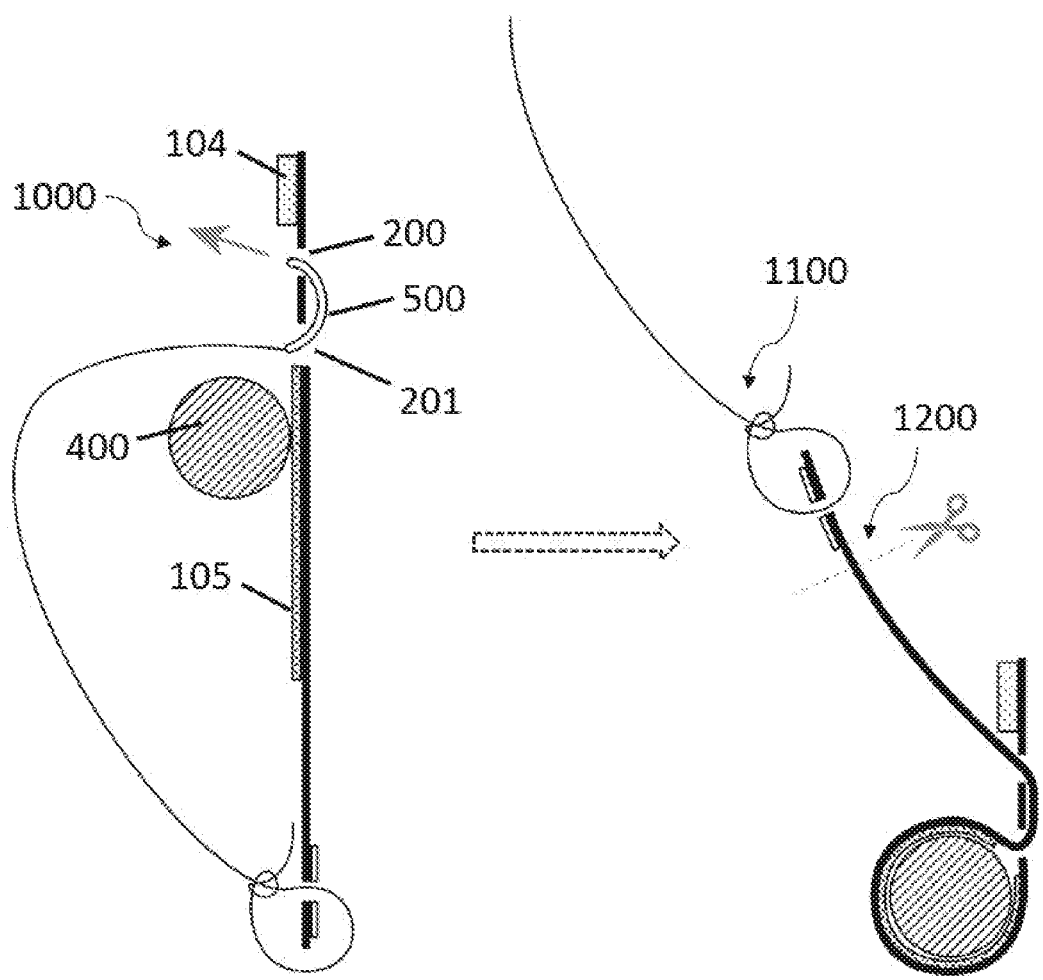
FIG. 10 depicts an exemplary method for fastening the cuff device of the invention around a tubular body structure by using surgical threads and blunt needles.

In one aspect according to the method of the invention, when the closing mechanism comprises multiple rings (106) these can be used one after another to close the cuff device multiple times. Advantageously, this configuration allows to easily move the implant from one location to another, e.g. from one position along a tubular structure (such as a nerve root) to another. According to this embodiment, a curved blunt needle (500) can pass (1000) easily through buckles (200, 201) and pull the device through said buckles in one motion. The working principle is that an operator, e.g. a surgeon, passes (1000) the needle (500) through a first ring (106) in a pre-cut hole and makes a knot (1100). He can then easily place the cuff device using the needle (500). Once done, the surgeon cut (1200) the implant between a first (106) and a second ring (106'). If the surgeon needs to remove and replace the implant, (s)he can redo the procedure using the second ring (106'). Once happy with the placement, the surgeon can cut all the rings to remove any hard part of the implant. FIGS. 9 and 10 show a multi-ring device and a schematics of the procedure as described above, exemplified with a single passage for the sake of an easier comprehension.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A cuff device comprising:
   a support having a first end, a second end, and an elongated body therebetween, the support being stretchable;
   a connection device for at least one of electrical, magnetic, and fluidic connection with an external device;
   a buckle configured to receive the first end of the support and configured for a slidable engagement with the elongated body to close and lock the cuff device at desired positions; and
   at least one of
   (i) at least one of an electrode and electronic component operatively connected with the connection device, the at least one of an electrode and electronic component configured to electrically interface with a biological tissue, and
   (ii) a channel having an inlet, an outlet, and an elongated body therebetween, the channel operatively connected with the connection device by the inlet and configured to fluidically interface with a biological tissue by the outlet.

2. The cuff device according to claim 1, wherein the electrode is stretchable.

3. The cuff device according to claim 1, further comprising:
   a reinforcement structure arranged at the first end of the support.

4. The cuff device according to claim 1, wherein at least one of the electrode and the channel of the outlet is located at the second end.

5. The cuff device according to claim 1, wherein at least one of the electrode and the channel of the outlet is located on the elongated body.

6. The cuff device according to claim 1, wherein the buckle is located at the second end of the support.

7. The cuff device according to claim 1, further comprising a second buckle.

8. The cuff device according to claim 7, wherein at least one of the electrode and the channel outlet are located on the second end of the support, between the buckle and the second buckle.

9. The cuff device according to claim 1, wherein the connection device is located at the second end of the support.

10. The cuff device according to claim 9, wherein the second end includes a lateral, elongated portion perpendicular to a longitudinal axis of the elongated body, and the connection device is located on the lateral, elongated portion.

11. The cuff device according to claim 1, wherein the connection device includes at least one of an electrically conductive element and a coil.

12. A system comprising the cuff device of claim 1, wherein the cuff device is operatively connected with the external device by the connection device.

13. The system of claim 12, wherein the external device includes one of an electro-stimulator, an electrical amplification system, an electrical recording system, a telemetric device, a syringe pump, a pressure-based pumping system, and a haemostatic pumping system.

14. The cuff device according to claim 1, wherein movement of the first end within the buckle causes the sliding of the elongated body.

15. A method for sensing a physiological signal or stimulating an electrical or pharmacological activity in a tubular body structure of a subject, the method performed with a cuff device, the cuff device including,
   a support having a first end, a second end, and an elongated body therebetween, the support being stretchable,
   a connection device for at least one of electrical, magnetic, and fluidic connection with an external device,
   at least one of (i) at least one of an electrode and electronic component operatively connected with the connection device, the at least one of an electrode and electronic component configured to electrically interface with a biological tissue, and (ii) a channel having an inlet, an outlet, and an elongated body therebetween, the channel operatively connected with the connection device by the inlet and configured to fluidically interface with a biological tissue by the outlet, and
   a buckle configured to receive the first end and configured for a slidable engagement with the elongated body to close and lock the cuff device at desired positions, the method comprising the steps of:
   inserting the first end of the cuff device into the buckle to wrap the cuff device around a tubular body structure of the subject; and
   sliding the elongated body within the buckle to close and lock the cuff device in a position permitting the tubular body structure to be contacted by at least one of the electrode and the outlet of the channel of the cuff device.

16. The method of claim 15, wherein the tubular body structure is one of a peripheral nerve, a CNS nerve, a gut structure, an oesophagus, a urethra, an ureter, and an artery.

17. The method of claim 15, further comprising the step of:
   sensing a physiological signal of the tubular body structure of the subject.

18. The method of claim 15, further comprising the step of:
   stimulating an electrical and/or pharmacological activity of the tubular body structure of the subject.

19. The method of claim 15, further comprising the step of:
   treating and/or diagnosing one or more pathological conditions of the subject.

* * * * *